US006972207B2

(12) United States Patent
Toyota et al.

(10) Patent No.: US 6,972,207 B2
(45) Date of Patent: Dec. 6, 2005

(54) METHOD OF MANUFACTURING ANNULAR OBLIQUE LIGHT ILLUMINATION APPARATUS AND FLEXIBLE WIRING SUBSTRATE

(75) Inventors: Makoto Toyota, Saitama (JP); Shin Toyoda, Tochigi (JP); Hitoshi Yoshida, Tochigi (JP)

(73) Assignee: Moritex Corporation, Tokyo (JP)

( * ) Notice: Subject to any disclaimer, the term of this patent is extended or adjusted under 35 U.S.C. 154(b) by 0 days.

(21) Appl. No.: 10/806,284

(22) Filed: Mar. 23, 2004

(65) Prior Publication Data

US 2004/0206968 A1 Oct. 21, 2004

(30) Foreign Application Priority Data

Mar. 24, 2003 (JP) .............................. 2003-079330

(51) Int. Cl.[7] .......................... G06K 9/00; M61G 13/00
(52) U.S. Cl. .............................. 438/24; 438/46; 362/3; 362/173; 348/86; 348/87; 385/901
(58) Field of Search ............................. 362/3, 173, 182, 362/227, 249–250; 382/100, 141, 147, 152; 385/901; 348/86–87; 438/24, 46

(56) References Cited

U.S. PATENT DOCUMENTS 5,920,643 A * 7/1999 White et al. ................. 382/141

FOREIGN PATENT DOCUMENTS

JP 2975893 9/1999

OTHER PUBLICATIONS

English Language Abstract of JP 2975893.

* cited by examiner

Primary Examiner—Nathan J. Flynn
Assistant Examiner—Thomas L. Dickey
(74) Attorney, Agent, or Firm—Greenblum & Bernstein, P.L.C.

(57) ABSTRACT

An annular oblique light illumination apparatus manufactured by using a flexible wiring substrate in which a plurality of arcuate zonal wiring patterns each in the form of a developed frustconical shape as a light emitting device arranging surface when cut along the pattern are serpiginously formed continuously to a base film of a predetermined shape, by setting and soldering light emitting devices to the arcuate zonal wiring patterns, cutting out the arcuate zonal wiring patterns to form light emitting device arrays and fixing the same to the arranging surface, whereby the wiring substrate can be supported reliably without using any special jig conforming the arcuate shape of the wiring patterns for mounting the light emitting devices, thereby improving the soldering operation efficiency, saving the troubles of exchange and handling of jigs and further, avoiding slackening or distortion of the wiring substrate even in a case of applying soldering by a flow soldering apparatus.

12 Claims, 6 Drawing Sheets

METHOD OF MANUFACTURING ANNULAR OBLIQUE LIGHT ILLUMINATION APPARATUS AND FLEXIBLE WIRING SUBSTRATE

BACKGROUND OF THE INVENTION

1. Field of the Invention

The present invention concerns a method of manufacturing an annular oblique light illumination apparatus having a frustconical inner circumferential surface as a light emitting device arranging surface, and a flexible wiring substrate used therefor.

2. Statement Related Art

Figure 2:
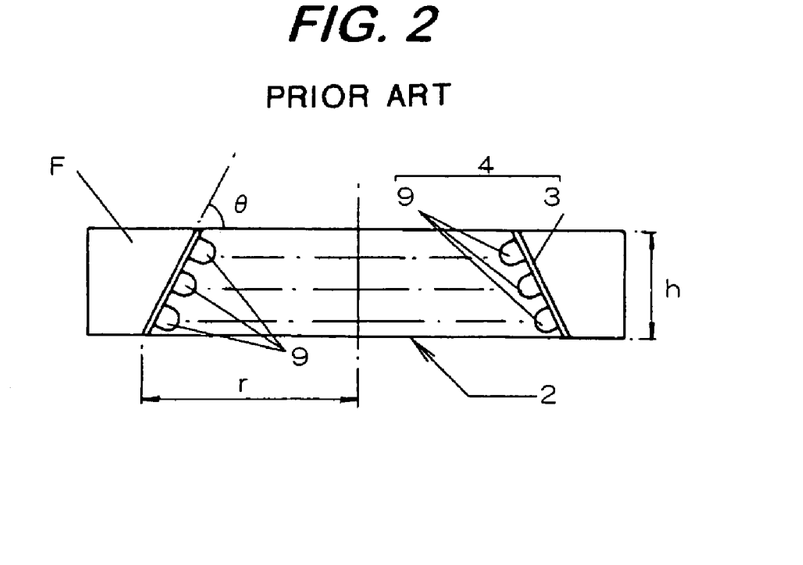
FIG. 2 is an explanatory view showing an annular oblique light illumination apparatus.

LED annular oblique light illumination apparatus are used, for example, in product inspection. In an existent LED annular oblique light illumination apparatus, as shown in FIG. 2, a light emitting device arranging surface 3 having a frustconical surface is formed inside an annular frame F, and a wiring substrate 41 having LED 9, 9, - - -, as light emitting device, mounted thereon is attached to the arranging surface 4.

Figure 9:
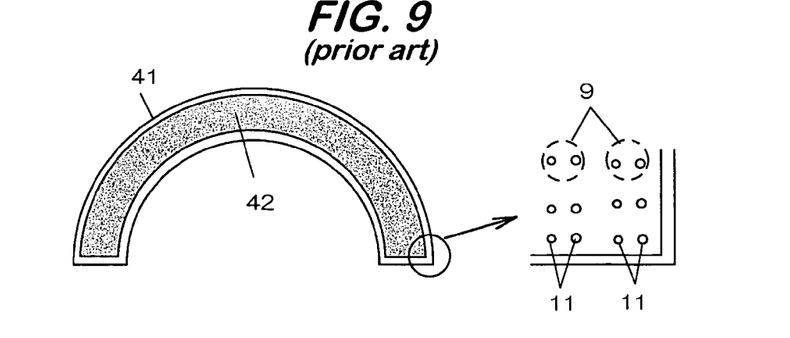
FIG. 9 is an explanatory view showing the prior art.

In a case of manufacturing an annular oblique light illumination apparatus 2 for a substrate, as shown in FIG. 9, an arcuate zonal flexible wiring substrate 41 conforming an arcuate zonal wiring pattern 42 is supported in a planar state, electrodes of LED 9, 9, - - - are inserted into through holes 11 therein and soldered, and then ends of the arcuate zonal flexible wiring substrate 41 are joined to each other to form a frustconical shape, which was then fixed to the arranging surface 3 (refer to Japanese Patent No. 2975893).

According to the constitution described above, since all LED 9, 9, - - - can be soldered at the same time by a flow soldering apparatus upon soldering while supporting the wiring substrate 41 in the planer state, this can save troublesome operation of soldering individual LED 9, 9, - - - .

However, for reliably supporting the arcuate zonal wiring substrate 41 in the planer state, it requires a special jig used exclusively therefor. In addition, since the arcuate zonal shape of the wiring pattern 42 is different depending on the diameter, width, and slanting of the arranging surface 3, jigs of shapes different on every arcuate zonal shapes have to be provided.

Further, upon automatic feeding of them to a flow soldering apparatus while fixing them on a conveyer or the like, since special jigs are necessary by the number of about several tens on every kinds of arcuate shapes in view of the production efficiency, a number of jigs have to be provided as a whole.

Further, in a case where operation of conducting soldering for a wiring substrate 41 of a certain shape has been completed and then soldering for another wiring substrate 41 of a different shape is started, it needs troublesome operation that all the jigs have to be exchanged.

Further, since the shape of the wiring substrate 41 is not symmetrical, the shape of the jig is also complicated. When the wiring substrate 41 is supported on a square frame it is slackened or distorted at not retained end edges by the weight of the LED 9,9 - - - , to result in a problem of soldering failure.

In view of the above, it is intended in the present invention to enable reliable support for a wiring substrate without using a special jig conforming the arcuate shape of a wiring pattern to which LEDs are mounted, thereby improving the operation efficiency of soldering, as well as saving the troublesome exchange and handling of jigs and, further, avoid occurrence of product deficiency even in a case of applying soldering by a flow soldering apparatus.

SUMMARY OF THE INVENTION

The foregoing subject can be attained in accordance with the present invention by a method of manufacturing an annular oblique light illumination apparatus having a frustconical inner circumferential surface as a light emitting device arranging surface, which comprises;

using a flexible wiring substrate in which a plurality of arcuate zonal wiring pattern parts for mounting light emitting devices each in the form of a developed frustconical shape are serpiginously formed continuously to a base film of a predetermined shape, inserting electrodes of light emitting devices into the arcuate zonal wiring pattern parts and soldering them then, cutting out the arcuate zonal wiring patterns to form a light emitting device arrays, and fixing each light emitting device array to the arranging surface.

According to the present invention, since a flexible wiring substrate in which arcuate zonal wiring patterns are formed continuously on a base film of a determined shape is normalized in accordance with the shape of a jig irrespective of the arcuate shape of the wiring pattern, there is no requirement for providing plural kinds of jigs.

In this case, when the base film is formed, for example, in a square shape, a general purpose square frame can be used as the jig and the manufacturing cost for the jig can be decreased.

Further, since the base film can be supported simply by merely stretching and setting the film and since the entire circumference thereof can be supported reliably, soldering failure is scarcely caused by the slackening or distortion of the wiring substrate.

Further, since a plurality of arcuate zonal wiring patterns for mounting light emitting devices are formed on one base film, the production efficiency is improved.

Further, since the wiring patterns are continued with each other directly or by way of a connection wiring pattern to form a serpiginous stripe wiring pattern, a circuit can be formed from one end to the other end thereof, and LED mounted to each of the patterns can be lit at the instance soldering is completed thereby enabling product inspection all at once.

PREFERRED EMBODIMENTS OF THE INVENTION

The present invention is to be described by way of the preferred embodiments referring to the accompanying drawings.

Figure 1:
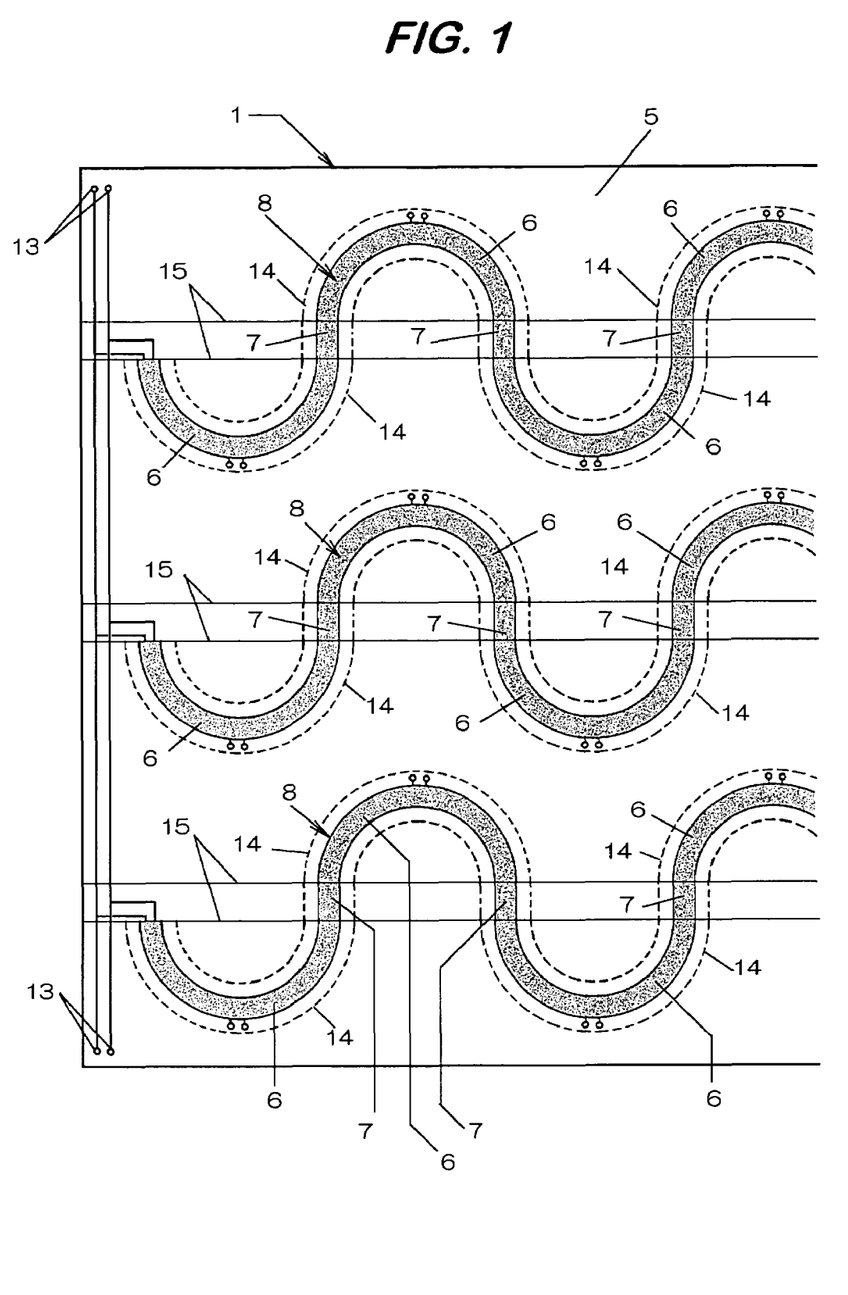
FIG. 1 is an explanatory view showing a flexible wiring substrate according to the present invention.

A flexible wiring substrate 1 shown in FIG. 1 is used for forming an LED array (light emitting device array) 4 attached to a light emitting device arranging surface 3 having a frustconical inner circumferential surface formed inside an annular frame F of an annular oblique light illumination apparatus 2 (refer to FIG. 2).

In the flexible wiring substrate 1, a plurality of arcuate zonal wiring patterns 6, 6, - - - for mounting light emitting devices each in the form of a developed frustconical shape when cut along the pattern are serpiginously formed continuously by way of connecting wiring patterns 7 to/on a base film 5 of a determined shape. Such serpiginous patterns, 8 are formed in a plurality of rows.

Figure 4:
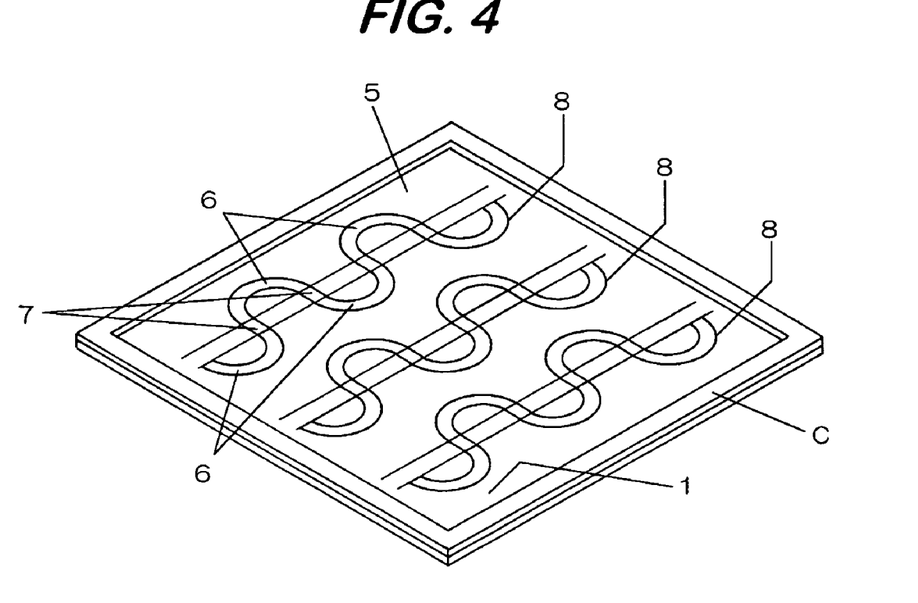
FIG. 4 is an explanatory view showing a portion of a manufacturing step.

The base film 5 used has normalized shape and size such that it can be attached, for example, to a carrier (jig) C of a flow soldering apparatus, for example, as shown in FIG. 4, irrespective of the shape of the arcuate zonal wiring pattern 6. In this embodiment, a substantially square film of a size capable of being mounted on a general purpose carrier used upon soldering a general purpose substrate is used.

Figure 3:
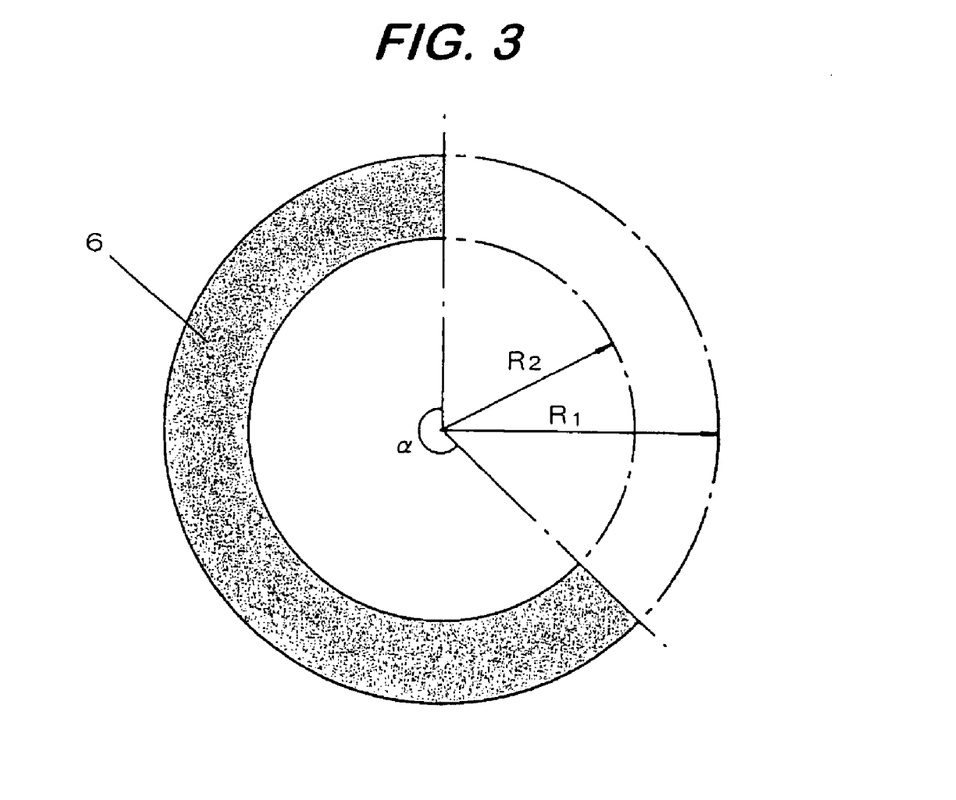
FIG. 3 is an explanatory view showing the dimension of an arcuate zonal pattern shape.

The shape of the arranging surface 3 and the shape of each of the arcuate zonal wiring patterns 6 are represented by the following relations:

$$R_1 = r/\cosine \theta \quad (1)$$

$$R_1 - R_2 = h/\sine \theta \quad (2)$$

$$r/R_1 = \alpha/2\pi \quad (3)$$

in which $\theta$ is an angle of inclination of the arranging surface 3, r is a radius for the opening at the bottom, and h is a height (refer to FIG. 2), and $R_1$ is an outer radius of the arcuate zonal wiring pattern 6, $R_2$ is an inner radius thereof, and $\alpha$ is the center angle (refer to FIG. 3).

For example, assuming the angle of inclination of the arranging surface 3 as: $\theta=60°$, the radius for the opening at the bottoms as: r=2.5 cm, the height as: h=1.5 cm, the arcuate zonal pattern is determined such as the outer radius of the arcuate zonal wiring pattern 6 as: $R_1=5$ cm, the inner radius thereof as: $R_2 \approx 3.3$ cm, and the center angle as: $\alpha=180°$.

Through holes 11 for inserting the electrodes 10 of LED (light emitting device) 9, 9, - - - are formed to the arcuate zonal wiring pattern 6, and a land 12 for soldering the electrode 10 is formed at the back for each of the through holes 11.

Each of the wiring patterns 6, 6 . . . is designed such that a closed circuit for inspection is established in a state of mounting LED 9, 9, - - - and inspection terminals 13 are formed to the base film 5.

Further, for easily cutting out the serpiginous pattern 8 simply from the base film 5, perforations 14 are formed along both sides of the pattern 8, and cut out lines 15 are drawn between the arcuate zonal wiring patterns 6 and the connecting wiring patterns 7.

In a case of manufacturing the annular oblique illumination apparatus 2 by using the flexible wiring substrate 1, as shown in FIG. 4, the flexible wiring substrate 1 is attached to the square frame-like carrier (jig) C in a stretched state.

Since the base film 5 for the flexible wiring substrate 1 is formed as a substantially square shape, the base film 5 can be reliably fixed by fixing at four sides while stretching the base film.

Further, since the base film 5 is normalized in accordance with the shape of the carrier C, one kind of the carrier C may suffice.

Then, electrodes of LED 9, 9, - - - are successively inserted into the through holes 11 of the arcuate zonal wiring pattern 6 and, after inserting LED 9, 9, - - - into all through holes 11, the electrodes 10 are soldered to the lands 12.

Figure 5:
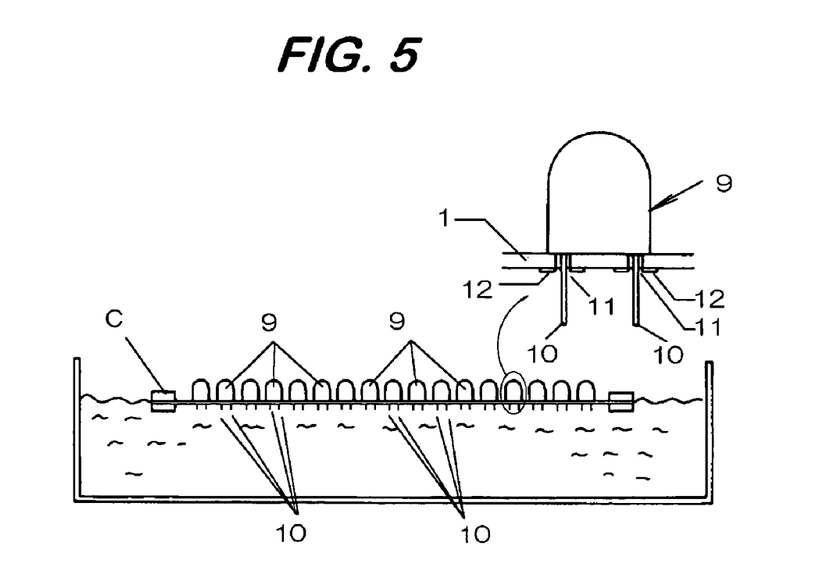
FIG. 5 is an explanatory view showing a portion of a manufacturing step.

In this case, as shown in FIG. 5, when the rear face of the wiring substrate 1 fixed to the carrier C is in contact with a solder liquid surface in a flow soldering apparatus, soldering can be conducted simply. In addition, since the base film 5 is reliably supported in a planar state under stretching, the arcuate zonal pattern 6 is neither slackened nor distorted irrespective of the weight of LED 9, 9, - - -, so that soldering failure is not caused thereby.

Then, at the instance, the LED 9, 9, - - - have been completed for mounting, when electric power is supplied from the inspection terminals 13 and when lighting up for the LED 9, 9, - - - is confirmed, a conduction inspection can be done for a plurality of the arcuate zonal wiring patterns 6 on every wiring substrate 1 simultaneously.

When all LED 9, 9, - - - are lit, since this indicates that all the patterns 6 have passed the conduction inspection, the test time can be shortened.

Further, if any one of the LED is not lit, since there may be considered a circuit failure or device failure, they may be sent to a re-inspection station for detailed inspection.

Then, when a portion of the arcuate zonal pattern 6 that has passed the conduction inspection is cut out, an arcuate zonal LED array 4 is formed.

In this case, the pattern may be cut along the perforations 14 formed on both sides of the serpiginous pattern by using pincers or cutters and the arcuate zonal pattern 6 and the connecting wiring patterns 7 may be cut out from the cut out lines 15. The perforations 14 may be formed by weakening the base film peelably, for example, using a radio frequency sewing machine or it may be a printed cut out lines.

Figure 6:
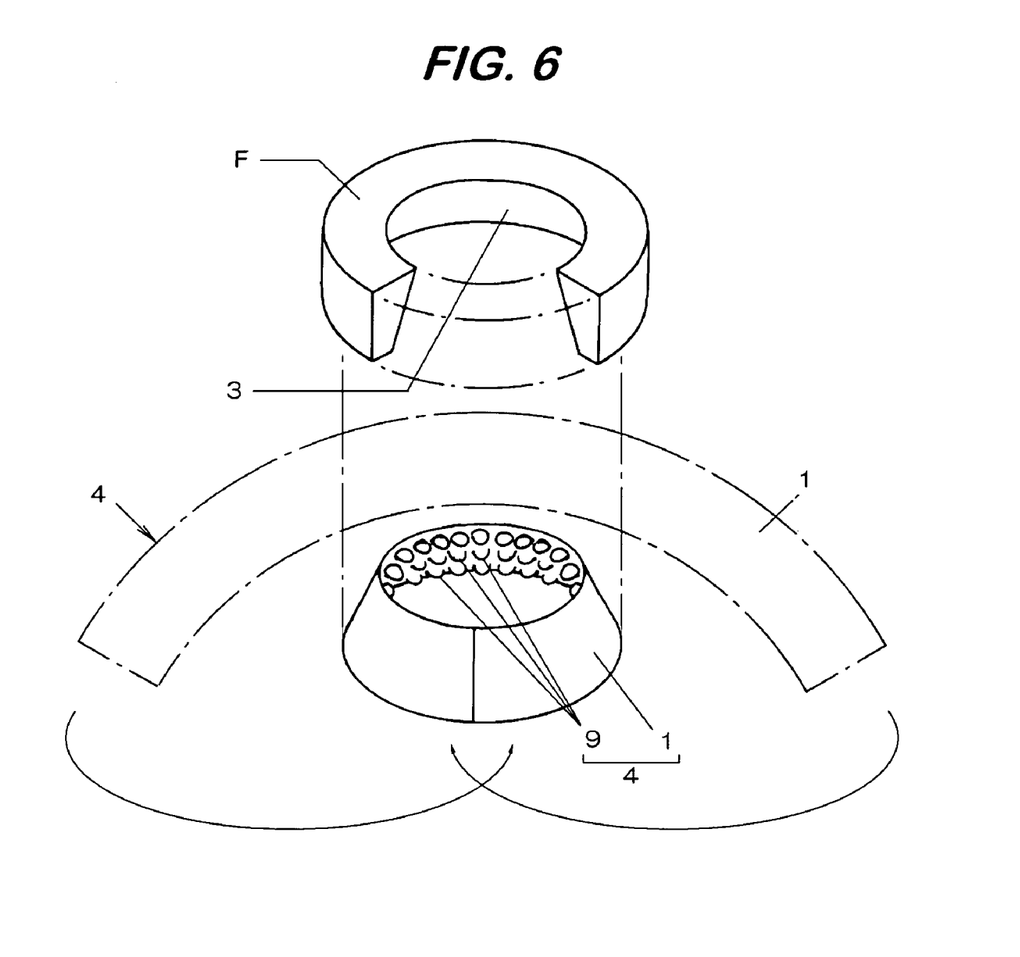
FIG. 6 is an explanatory view showing a portion of a manufacturing step.

Finally, as shown in FIG. 6, when the ends of the arcuate zonal pattern 6 are connected to each other, since the LED array 4 forms a frustconical shape, it is fixed to the light emitting device arranging surface 3 and necessary electric connection is applied to complete the annular oblique light illumination apparatus 2.

Figure 7:
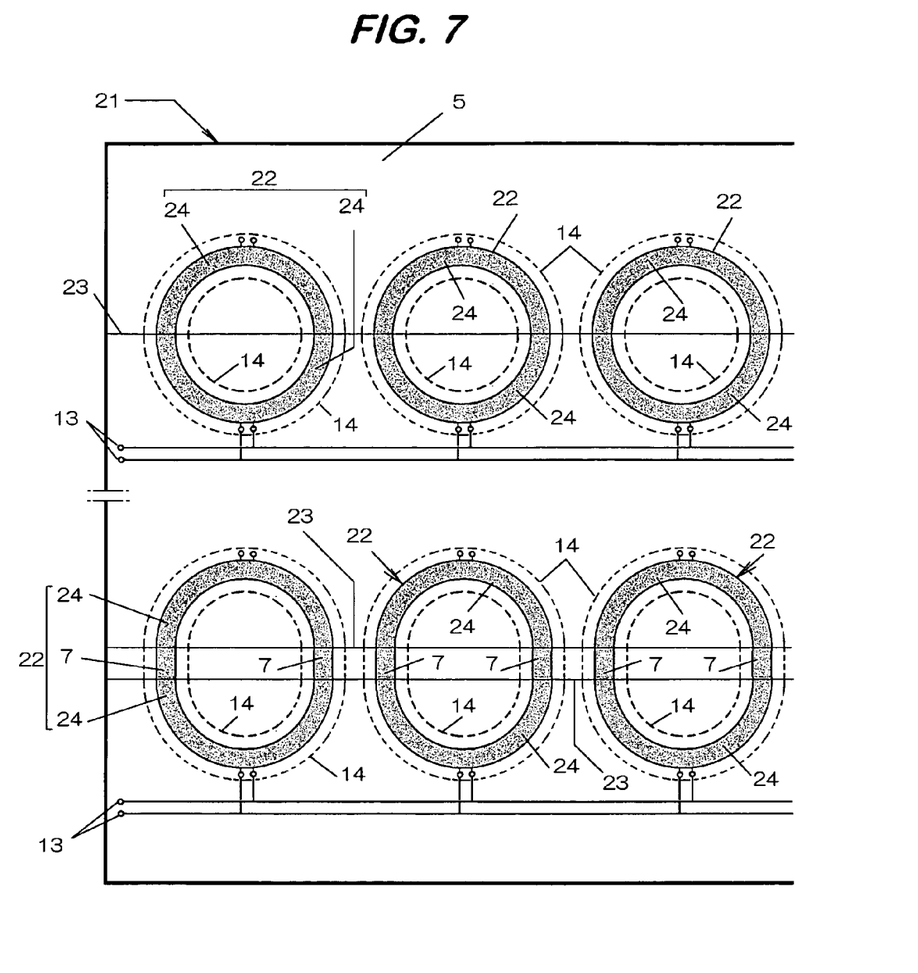
FIG. 7 is an explanatory view showing another flexible wiring substrate.

FIG. 7 shows another flexible wiring substrate according to the invention. Those portions identical with FIG. 1 carry same reference numerals for which detailed explanations will be omitted.

In a flexible wiring substrate 21 of this embodiment, a plurality of annular stripe wiring patterns 22 for mounting light emitting devices each in the form of an arcuate shape that can be mounted to the LED arranging surface 3 when cut at a predetermined center angle $\alpha$ are formed to a predetermined square base film 5.

The annular stripe pattern 22 may be a circular or elliptic shape. In a case where the angle of inclination of the arranging surface 3 is, for example, $\theta=60°$, since the center angle is: $\alpha=180°$, they may be opposed to each other as a circular shape, or as an elliptic shape by way of a connecting wiring pattern 7. When it is cut along the cut out line 23 and the perforations 14, one annular stripe wiring pattern 22 is divided into two arcuate zonal parts 24.

The annular oblique light illumination apparatus 2 can be manufactured by using the flexible wiring substrate 21 in the same manner as described above by fixing the wiring substrate 21 to the carrier C, inserting the electrodes 10 of LED 9, 9, - - - into the through holes 11 formed to the arcuate zonal parts 24 of the wiring pattern 22, soldering the electrodes 10 to the wiring pattern 22, then supplying electric power from the inspection terminals 13 to effect conduction inspection, then cutting out the arcuate zonal part 24 mounted with LED 9, 9, - - - to form an LED array 4, connecting the ends of the LED array 4 to each other into a frustconical shape and fixing the same to the LED arranging surface 3.

Figure 8:
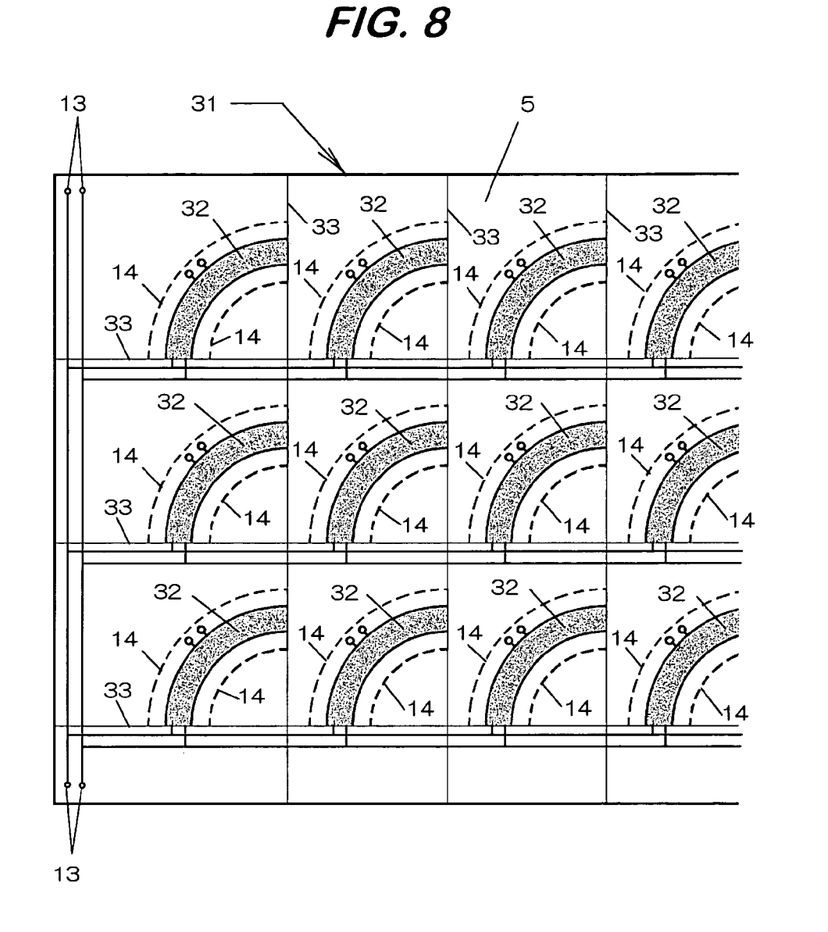
FIG. 8 is an explanatory view showing other flexible wiring substrate.

Further, FIG. 8 shows other wiring substrate according to the invention. Those portions identical with FIG. 1 carry same reference numerals for which detailed descriptions are to be omitted.

In the flexible wiring substrate 31 of this embodiment, one or more arcuate zonal wiring patterns 32 for mounting light emitting devices each in the form of a developed frustconical shape of the arranging surface 3 when cut along cut out lines 33 and perforations 14 are formed to a predetermined square base film 5. Each of the arcuate zonal wiring patterns 32 is formed so as to have a center angle α of about 90° in a case where the angle θ of inclination of the arranging surface is 75°.

The annular oblique light illumination apparatus 2 can be manufactured by using the flexible wiring substrate 31 in the same manner as described above, by attaching the wiring substrate 31 to the carrier C, inserting the electrodes 10 of LED 9, 9, - - - into the through holes 11 formed in the wiring pattern 32, soldering the electrodes 10 to the wiring pattern 32, then supplying electric power from the inspection terminals 13 to apply conduction inspection, cutting out the wiring pattern 32 mounted with LED 9, 9, - - - to form the LED array 4, connecting the ends of the LED array 4 to each other into a frustconical shape and fixing the same to the LED arranging surface 3.

In any of the printed wiring substrates 21 and 31 shown in FIG. 7 and FIG. 8, since the base film is formed into a substantially square shape, four sides thereof can reliably be fixed by the carrier C.

Further, since the base film 5 has a predetermined shape having no concern with the shape of the annular zonal wiring pattern 22 or the arcuate zonal wiring pattern 32, one kind of jig may suffice also in a case of fixing the same by using the jig.

Further, when soldering is applied by bringing the rear face of the wiring substrate 21 or 31 into contact with the solder liquid surface in the flow soldering apparatus, since the base film 5 is firmly supported in a stretched state, the annular zonal wiring pattern 22 or the arcuate zonal wiring pattern 32 is neither slackened nor distorted even by the weight of LED 9, 9, - - - and soldering failure is not caused thereby.

The foregoing descriptions have been made to a case of applying soldering by the flow soldering apparatus, but the invention is not restricted only thereto and can also provide an advantageous effect of providing good operation efficiency even in a case of manual soldering since the wiring substrate 1 can be fixed easily.

As has been described above according to the present invention, since the wiring substrate of a predetermined shape, for example, a square shape formed with arcuate zonal wiring patterns is used instead of using the arcuate zonal wiring substrate and the wiring substrate can be supported reliably using only one kind of the jig irrespective of the shapes of the wiring patterns, troublesome exchange or handling of jigs can be saved. In addition, since the wiring substrate is less slackened or distorted upon soldering by using the flow soldering apparatus, it can provide an excellent effect of not resulting in product deficiency caused by soldering failure.

The present disclosure relates to subject matter contained in Japanese Patent Application No. 2003-79330, filed on Mar. 24, 2003, the contents of which are herein expressly incorporated by reference in its entirety.

What is claimed is:

1. A method of manufacturing an annular oblique light illumination apparatus having a frustoconical inner circumferential surface as a light emitting device arranging surface, the method comprising:
    providing a flexible wiring substrate, on which a plurality of arcuate zonal wiring patterns for mounting light emitting devices, each in the form of a developed frustconical shape, are serpiginously formed continuously on a base film having a quadrangular shape;
    inserting electrodes of the light emitting devices into the arcuate zonal wiring patterns and soldering the electrodes to the arcuate zonal wiring patterns;
    cutting out the arcuate zonal wiring patterns from the base film to form light emitting device arrays; and
    fixing each light emitting device array to the arranging surface.

2. The method according to claim 1, wherein the base film has a substantially square shape.

3. The method according to claim 1, further comprising providing cutting guide lines on the base film.

4. The method according to claim 1, further comprising providing inspection terminals on the base film configured to enable testing of the mounting of the light emitting diodes to the arcuate zonal wiring patterns.

5. A method of manufacturing an annular oblique light illumination apparatus having a frustoconical inner circumferential surface as a light emitting device arranging surface, the method comprising:
    providing a flexible wiring substrate, on which one or more annular stripe wiring patterns for mounting light emitting devices, each in the form of a developed frustoconical shape when cut for a predetermined center angle, are formed on a base film having quadrangular shape;
    inserting electrodes of the light emitting devices to the annular stripe wiring patterns corresponding to the center angle and soldering the electrodes to the base film;
    cutting out the annular stripe wiring patterns from the base film to form light emitting device arrays; and
    fixing each light emitting device array to the arranging surface.

6. The method according to claim 5, wherein the base film has a substantially square shape.

7. The method according to claim 5, further comprising providing cutting guide lines on the base film.

8. The method according to claim 5, further comprising providing inspection terminals on the base film configured to enable testing of the mounting of the light emitting diodes to the annular stripe wiring patterns.

9. A method of manufacturing an annular oblique light illumination apparatus having a frustoconical inner circumferential surface as a light emitting device arranging surface, the method comprising:
    providing a flexible wiring substrate, on which one or more arcuate zonal wiring patterns for mounting light emitting devices, each in the form of a developed frustoconical shape, are formed on a base film having quadrangular shape;

inserting electrodes of the light emitting devices into the arcuate zonal wiring patterns and soldering the electrodes to the base film;

cutting out the arcuate zonal wiring patterns to form light emitting device arrays; and fixing each light emitting device array to the arranging surface.

10. The method according to claim 9, wherein the base film has a substantially square shape.

11. The method according to claim 9, further comprising providing cutting guide lines on the base film.

12. The method according to claim 9, further comprising providing inspection terminals on the base film configured to enable testing of the mounting of the light emitting diodes to the arcuate zonal wiring patterns.

* * * * *